United States Patent [19]
Nakanishi et al.

[11] Patent Number: 5,739,014
[45] Date of Patent: Apr. 14, 1998

[54] POLYSACCHARIDE, PROCESS FOR PRODUCTION THEREOF, USE THEREOF, AND AGROBACTERIUM RADIOBACTER TNM2 STRAIN

[75] Inventors: Osamu Nakanishi, Ibaraki; Yoichi Ooiso, Higashiosaka; Takeshi Okumiya, Yao; Ryosuke Sugihara, Osaka; Kaoru Kawashima, Habikino; Akira Misaki, Ashiya; Masahira Nakagawa, Takatsuki, all of Japan

[73] Assignee: Tayca Corporation, Osaka, Japan

[21] Appl. No.: 586,921

[22] PCT Filed: Jun. 1, 1995

[86] PCT No.: PCT/JP95/01074

§ 371 Date: Apr. 12, 1996

§ 102(e) Date: Apr. 12, 1996

[87] PCT Pub. No.: WO95/33066

PCT Pub. Date: Dec. 7, 1995

[30] Foreign Application Priority Data

Jun. 1, 1994  [JP]  Japan ................... 6-142369

[51] Int. Cl.$^6$ .............. C12P 19/04; C07G 17/00; C07H 1/00; C07H 3/00

[52] U.S. Cl. .............. 435/101; 536/123; 536/123.1; 435/822; 514/54

[58] Field of Search ............... 536/123, 123.1; 435/101, 822; 574/54

*Primary Examiner*—Sheela Huff
*Attorney, Agent, or Firm*—David G. Conlin; Peter F. Corless; Dike, Bronstein, Roberts & Cushman, LLP

[57] ABSTRACT

A polysaccharide having a molecular weight of about $5 \times 10^3$ to $10 \times 10^6$ as measured by gel permeation chromatography and composed of 5 saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight.

12 Claims, 2 Drawing Sheets

POLYSACCHARIDE, PROCESS FOR PRODUCTION THEREOF, USE THEREOF, AND AGROBACTERIUM RADIOBACTER TNM2 STRAIN

FIELD OF ART

The present invention relates to a novel polysaccharide, a process for the preparation thereof, a use of the novel polysaccharide, and a novel strain having an ability to produce such a polysaccharide. The novel polysaccharide of the present invention can be used in many fields of industry and for various purposes. For instance, it can be used as a gelatinizer, humectant, film forming agent, emulsifier, foam stabilizer, water retaining agent, cement admixture and the like.

BACKGROUND ART

Many polysaccharides such as gellan gum, curdlan, hyaluronic acid, xanthan gum and pullulan, have been produced by use of microorganisms. Of these polysaccharides, only gellan gum and curdlan have been practically utilized as a gelatinizer in the fields of foods and related products.

Japan Patent Application Laid-Open (Kokai) 63-156707 proposes cosmetics containing hyaluronic acid as humectant. This humectant can serve for protecting the skin from external stimulus or toughening of skin surface and is also instrumental in bettering the feeling of use of cosmetics. It is generally considered desirable that a humectant be contained in cosmetics in such an amount that the cosmetics will have a moisture retention in a range of 10–50% under the ordinary environmental condition with a relative humidity of 40–80%. It is also required of the cosmetic humectant that its moisture retaining ability is little affected by the change of relative humidity in the ambient atmosphere (see Fragrance Journal, extra edition No. 9 "Science of Humectant", 1988, p. 34, etc.).

The gelatinizers comprising gellan gum or curdlan have drawbacks noted as follows. That is, gellan gum decomposes under an alkaline condition, and also gelatinized gellan gum is dissolved and degraded when left under an alkaline condition at room temperature. Curdlan has a problem that its gel tends to release water. Also, the humectants comprising hyaluronic acid have a serious disadvantage that their moisture retainability is unstable as it is susceptible to the ambient humidity.

In the course of researches for a material having excellent gelation characteristics and moisture retainability, the present inventors have found that the novel polysaccharide obtained by use of a newly discovered microorganism has a property of alkali resistance, can form a gel with low water releasing tendency, and also has an excellent moisture retainability which is scarcely affected by relative humidity in the ambient atmosphere. It has also been found that this novel polysaccharide has other useful properties.

DISCLOSURE OF THE INVENTION

The present invention has been attained on the basis of the above finding, and the object of the present invention is to provide a novel polysaccharide and a process for preparing the same.

Another object of the present invention is to provide pertinent uses of the novel polysaccharide.

Still another object of the present invention is to provide a novel microorganism belonging to the genus Agrobacterium.

The above objects can be attained by the following embodiments of the present invention:

(1) A novel polysaccharide having a molecular weight of about $5\times10^3$ to $10\times10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6: 0.5–1.7:0.5–1.7, with the content of o-acetyl groups in the polysaccharide being 0–10% by weight.

(2) A process for preparing a polysaccharide which comprises culturing a microorganism belonging to the genus Agrobacterium having an ability to produce a polysaccharide composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups being 0–10% by weight, and collecting from the culture the polysaccharide composed of 5 different saccharides, viz. D-glucose, D-galactose, D-glucuronic acid, D-ribose and D-riburonic acid in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight.

(3) A gelatinizer comprising a polysaccharide having a molecular weight of about $5\times10^3$ to $10\times10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid =10:1.8–2.9:1.8–2.6:0.5–1.7:0.5–1.7, with the content of o-acetyl in the polysaccharide groups being 0–10% by weight.

(4) A humectant comprising a polysaccharide having a molecular weight of about $5\times10^3$ to $10\times10^6$ in the polysaccharide and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide groups being 0–10% by weight.

(5) A film forming agent comprising a polysaccharide having a molecular weight of about $5\times10^3$ to $10\times10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide groups being 0–10% by weight.

(6) An emulsifier comprising a polysaccharide having a molecular weight of about $5\times10^3$ to $10\times10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid =10:1.8–2.9:1.8–2.6:0.5–1.7:0.5–1.7, with the content of o-acetyl groups in the polysaccharide being 0–10% by weight.

(7) A foam stabilizer comprising a polysaccharide having a molecular weight of about $5 \times 10^3$ to $10 \times 10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid =10:1.8–2.9:1.8–2.6:0.5–1.7:0.5–1.7, with the content of o-acetyl groups in the polysaccharide being 0–10% by weight.

(8) A water retaining agent comprising a polysaccharide having a molecular weight of about $5 \times 10^3$ to $10 \times 10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight.

(9) A cement admixture comprising a polysaccharide having a molecular weight of about $5 \times 10^3$ to $10 \times 10^6$ as measured by gel permeation chromatography and composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid =10:1.8–2.9:1.8–2.6:0.5–1.7:0.5–1.7, with the content of o-acetyl groups in the polysaccharide being 0–10% by weight.

(10) Agrobacterium radiobacter TNM-2 strain (FERM BP-4393) or its variants having an ability to produce polysaccharides.

The more detail of the present invention is explained below.

First, the novel polysaccharide provided according to the present invention is explained.

The polysaccharide of the present invention composed of 5 different saccharides, viz. D-glucose, D-galactose, D-glucuronic acid, D-ribose and D-riburonic acid, in a molar ratio of D-glucose:D-galactose:D-glucuronic acid: D-ribose:D-riburonic acid= 10:1.8–2.9:1.8–2.6:0.5–1.7:0.5–1.7, with the content of o-acetyl groups in the polysaccharide being 0–10% by weight.

The molecular weight of the polysaccharide of this invention which is determined by gel permeation chromatography is approximately $5 \times 10^3$ to $10 \times 10^6$. More specifically, in the present invention, the molecular weight was determined by using a high-speed-high performance liquid chromatograph of GPC mode with a column of "Asahipak GFA-7MF" (mfd. by Asahi Chemical Industry Co., Ltd.), using a 0.1M NaNO$_3$ solution as mobile phase, and applying a molecular weight-retention time calibration drawn up using pullulan of a known molecular weight as standard sample.

The polysaccharide of the present invention has the following properties.

(1) State

White fibrous (after freeze-dried).

(2) Solubility

Soluble in water, dilute acid, dilute alkali and dimethylsulfoxide, and insoluble in methanol, ethanol and acetone.

(3) UV absorption spectrum

Figure 1:
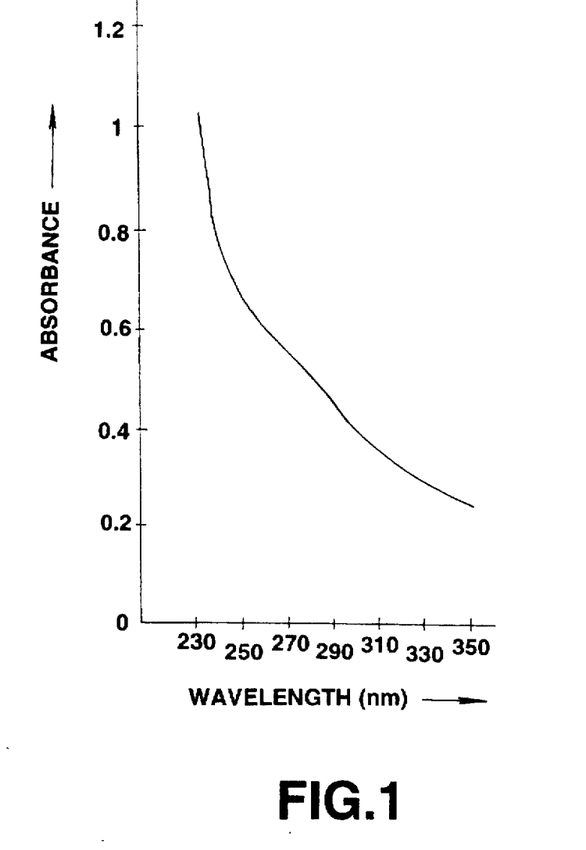
FIG. 1 shows an UV absorption spectrum of the polysaccharide according to the present invention.

UV absorption spectrum was measured in the atmosphere using a quartz cell with a light path length of 10 mm, placing a 0.5% (w/v) polysaccharide aqueous solution in the sample cell and water in the reference cell. The results of measurement are shown in FIG. 1. As is seen from FIG. 1, the absorptions of 280 nm and 260 nm corresponding to the specific absorption of protein (peptide) and nucleic acid, respectively are not observed.

(4) IR absorption spectrum

Figure 2:
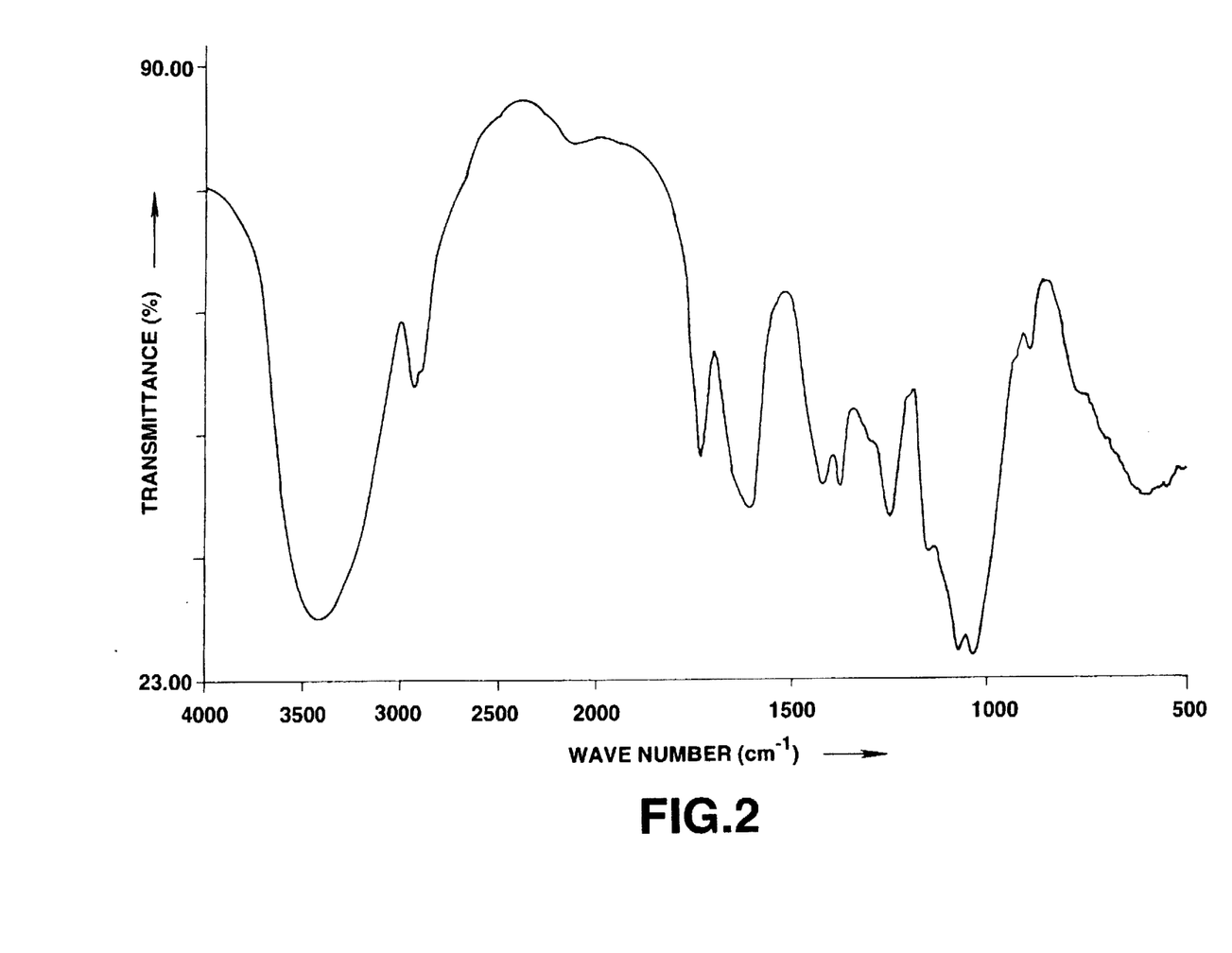
FIG. 2 shows an IR absorption spectrum of the polysaccharide according to the present invention.

IR absorption spectrum was measured according to the KBr tablet method. The results thereof are shown in FIG. 2. As is seen from FIG. 2, the absorptions of around 3400 cm$^{-1}$, 1620 cm$^{-1}$, 1730 cm$^{-1}$, 1250 cm$^{-1}$ and 2950 cm$^{-1}$ are observed corresponding to hydroxyl group, carboxyl group of uronic acid, o-acetyl group ether linkage, alkane group, respectively.

(5) Color reaction

The phenol sulfuric acid reaction, carbazole sulfuric acid reaction and m-phenylphenol reaction were positive.

Positive phenol sulfuric acid reaction means the presence of saccharides, and positive carbazole sulfuric acid reaction and positive m-phenylphenol reaction mean the presence of uronic acid. These results confirm that the polysaccharide of the present invention is an acidic polysaccharide containing uronic acid.

(6) Constituent saccharides and their contents (i) The polysaccharide of the present invention deacetylated by a dilute alkali (0.01M KOH) treatment was subjected to acid hydrolysis using 2M trifluoroacetic acid (TFA) at 100° C. for 6 hours and then derived to alditol acetate. Each of the obtained derivatives was analyzed by gas chromatography using ECNSS-Mcoated column "Gaschrom Q" (mfd. by Wako Pure Chemical Co., Ltd.). Consequently, there were detected the same compounds to that obtained from D-galactose and D-glucose as starting materials.

Also, after subjecting the polysaccharide of the present invention to said acid hydrolysis and fluorescence labeling with pyridylamino, the liquid chromatographic analysis was carried out with a column of TSKgel Sugar AX1 (mfd. by Toyo Soda Co. Ltd.), using a 1:9 mixture of CH$_3$CN and 0.7M K$_3$BO$_3$ (pH 9.0) as mobile phase. In this case, too, there were detected the same compounds to that obtained from D-galactose and D-glucose as starting materials. By these analytical results, it was found that the neutral sugars constituting the polysaccharide of the present invention were D-galactose and D-glucose, and it was determined by the calibration drawn by using D-galactose and D-glucose as standard materials that the contents of D-galactose and D-glucose in the polysaccharide of the present invention were 10–18% by weight and 48–67% by weight, respectively.

(ii) The polysaccharide of the present invention deacetylated by a dilute alkali (0.01M KOH) treatment was subjected to acid hydrolysis at 100° C. for 12 hours using 88% formic acid, then further subjected to acid hydrolysis under the same conditions as in (i) described above. After fluorescence labeling with dansylhydrazine, the specimen was analyzed by liquid chromatography with a column of Shim-pack CLC-NH2 (M) (mfd. by Shimadzu Corp.) using a 2:9 (v/v) mixture of 0.1M potassium acetate buffer (pH 5.6) and acetonitrile as mobile phase. As a result, there was detected only the same compound as that obtained from D-glucuronic acid as a starting material, and it was confirmed that glucuronic acid is only present as an uronic acid in the polysaccharide of the present invention, and no other uronic acids such as galacturonic acid are contained. By use of the calibration determined by using D-glucuronic acid, the D-glucuronic acid content in the polysaccharide of the present invention was 12–17% by weight.

(iii) The polysaccharide of the present invention deacetylated by a dilute alkali (0.01M KOH) treatment was subjected to acid hydrolysis at 100° C. for 4 hours using a solution adjusted to pH 2 with 1M sulfuric acid and then the specimen was analyzed by high-speed-high performance liquid chromatography with a column of Shimpack SCR-101N (mfd. by Shimadzu Corp.) using 10 mM sodium dihydrogenphosphate (adjusted to pH 2.5 with phosphoric acid) as mobile phase. The result confirmed that the polysaccharide of the present invention contained D-ribose and an unidentified substance beside the components found in (i) and (ii) described above. By using of the calibration drawn by using D-ribose, the D-ribose content in the polysaccharide of the present invention was 2.1–7.8% by weight.

For the identification of the unidentified substance, the polysaccharide of the present invention deacetylated by a dilute alkali (0.01M KOH) treatment was subjected to acid hydrolysis and the treatment of high-speed-high performance liquid chromatography under the above-described conditions to separate the unidentified substance. The separated unidentified substance was derived to N-propylaldoneamide acetate. The gas chromatographic analysis and gas chromatography-mass spectral analysis of the obtained derivative were carried out using a capillary column "SP-2380" (mfd. by SUPELCO SEPARATIONS TECHNOLOGIES GROUP (DIVISION OF ROHM AND HAAS). There was detected the same compound as that obtained from ribonic acid as a starting material, and it was confirmed that the unidentified substance was ribonic acid, riburonic acid or uronic acid-type of ribulose.

The unidentified substance was then subjected to fast atom bombardment mass spectrometry, which showed a molecular ion $(M^++1)$ peak at 165. Also, the $^1$H-NMR spectral analysis of the unidentified substance showed a peak (at around 5 ppm) attributing to anomer hydrogen. From these results, the unidentified substance was identified as D-riburonic acid. Also, the D-riburonic acid content in the dilute alkali-deacetylated polysaccharide of the present invention was 2.4–8.4% by weight, the remainder of deduction of the contents of D-glucose, D-galactose, D-glucuronic acid and D-ribose from the whole composition.

It was thus confirmed that the contents of the respective constituent carbohydrates of the polysaccharide of the present invention which was deacetylated by a dilute alkali (0.01M KOH) treatment were as follows: D-glucose= 48–67% by weight; D-galactose=10–18% by weight; D-glucuronic acid=12–17% by weight; D-ribose=2.1–7.8% by weight; D-riburonic acid=2.4–8.4% by weight, and that the molar ratio of said components was as follows: D-glucose:D-galactose:D-glucuronic acid:D-ribose:D-riburonic acid=10:1.8–2.9:1.8–2.6:0.5–1.7:0.5–1.7.

(7) Content of o-acetyl groups

The polysaccharide of the present invention was deacetylated in an aqueous solution of 0.01M potassium hydroxide and 0.13M potassium chloride at room temperature for 6 hours. The thus prepared specimen was subjected to high-speed liquid chromatographic analysis with a column of "Shim-pack CLC-DS (M)" (mfd. by Shimadzu corp.) using 10 mM potassium dihydrogenphosphate (adjusted to pH 2.3 with phosphoric acid) as mobile phase. As a result, there was detected a peak with the same retention time as the peak detected in the similar analysis of an aqueous solution of potassium acetate. From the previously drawn calibration and the peak height, the o-acetyl group content in the polysaccharide of the present invention was about 0–10% by weight based on the whole composition.

The o-acetyl group content in the polysaccharide of the present invention differs depending on the method for the purification of the polysaccharide from the culture. Specifically, the said content varies according to the duration, pH and other processing conditions of the alkali treatment. In the IR absorption spectrum of the deacetylated polysaccharide, the peak of around 1730 $cm^{-1}$ disappeared.

In view of the above properties, the polysaccharide of the present invention was confirmed to be an acidic heteropolysaccharide composed of D-glucose, D-galactose, D-glucuronic acid, D-ribose and D-riburonic acid in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight.

Since there exists no known polysaccharide composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, the polysaccharide of the present invention was confirmed to be a novel acidic heteropolysaccharide.

A process for preparing the polysaccharide according to the present invention is described below.

The process of the present invention comprises the steps of culturing a microorganism belonging to the genus Agrobacterium and having an ability to produce a polysaccharide composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight, and collecting from the culture the objective polysaccharide that is, a polysaccharide composed of 5 different saccharides, viz. D-glucose, D-galactose, D-glucuronic acid, D-ribose and D-riburonic acid, in a molar ratio of D-glucose:D-galactose:D-glucuronic acid:D-ribose:D-riburonic acid= 10:1.8–2.9:1.8–2.6:0.5–1.7:0.5–1.7, with the content of o-acetyl groups in the polysaccharide being 0–10% by weight. The molecular weight of the obtained polysaccharide determined by gel permeation chromatography is as usual approximately $5 \times 10^3$ to $10 \times 10^6$.

In a preferred embodiment of the present invention, a strain of Agrobacterium radiobacter having an ability to produce the said polysaccharide, specifically an Agrobacterium radiobacter TNM-2 strain (FERM BP-4393) or its variant, is used as the microorganism. Such a variant can be produced by a known mutagenetic means, for example, exposure to radiations such as ultraviolet rays or X-rays, or application of a chemical mutagen such as ethylmethanesulfonic acid (EMS) or N-methyl-N'-nitro-N-nitrosoguanidine (MNNG). The ability of a strain to produce the said polysaccharide can be determined by the analysis of the culture of the strain.

The bacteriological properties of the Agrobacterium radiobacter TNM-2 strain are listed in Tables 1–4.

TABLE 1

| Form | Asporogenic bacillus, slightly colloidal colony |
|---|---|
| Gram-stain | − |
| Glucose OF | O type |
| Motility | + |
| Flagellum | 1–2 |
| Catalase | + |
| Oxidase | + |

TABLE 2

| | |
|---|---|
| Growth in MacConkey's agar | − |
| Growth in SS agar | − |
| Growth in KCN agar | − |
| Utilization of citrate | + |
| Nitrate reduction | − |
| Generation of gas from nitrate | − |
| Growth in no-nitrogen medium | − |

TABLE 3

| Generation of acids from carbohydrates | |
|---|---|
| Glucose | + |
| Lactose | + |
| Maltose | + |
| Mannitol | + |
| Salicin | + |
| Sucrose | + |
| Xylose | + |
| Fructose | + |
| Inositol | + |
| Cellobiose | + |
| Trehalose | + |
| Galactose | + |

TABLE 4

| | |
|---|---|
| Casein hydrolysis | − |
| Gelatin hydrolysis | − |
| Starch hydrolysis | − |
| Urease | + |
| VP | − |
| Indole | − |
| ONPG | + |
| Lysine decarboxylase | − |
| Alginine dihydrolase | − |
| Ornithine decarboxylase | − |
| Esculin hydrolysis | + |
| Tween 80 hydrolysis | − |
| LV | − |
| Specified extracellular | + | polysaccharide-produced (ability to produce a polysaccharide having a specified molar ratio of constituent saccharides, viz. D-glucose:D-galactose:D-glucuronic acid:D-ribose:D-riburonic acid= 10:1.8–2.9:1.8–2.6:0.5–1.7:0.5–1.7)

From the above bacteriological properties, the strain of the present invention has been ascertained as belonging to the genus Agrobacterium. Reviewing these properties in comparison with the data given in Bergey's Manual of Systematic Bacteriology, Vol. 1, 254, 1984, although no mention of specified extracellular polysaccharide-produced of the type culture Agrobacterium radiobacter is described, it was found that the properties of the strain of the present invention well agreed with the data disclosed in the above literature. From these facts, the strain of the present invention was considered as a variant of Agrobacterium radiobacter, and it was named Agrobacterium radiobacter TNM-2 strain.

The strain of the present invention was deposited at the Patented Microorganism Deposit Center (1-1, Higashi 1-chome, Tsukuba-shi, Ibaraki-ken, 305 Japan) of the National Institute of Bioscience and Human Technology, the Agency of Industrial Science and Technology, the Ministry of International Trade and Industry, Japan under Accession No. FERM BP-4393 at the date of Aug. 25, 1993.

The culture medium for said microorganism used in the process of the present invention is not specifically defined as far as it is capable in the culture medium to grow the microorganisms belonging to the genus Agrobacterium and the culture medium contains appropriate amounts of a carbon source, a nitrogen source, inorganic salts and micronutrients. Carbon sources usable in the present invention include glucose, galactose, fructose, xylose, mannitol, sucrose, trehalose, glucuronic acid, galacturonic acid and the like. Nitrogen sources include nitrates, ammonium salts, synthetic compounds such as urea, etc., and natural organic substances such as polypeptone, corn steep liquor, yeast extract, meat extract, defatted soybean extract, peptide, amino acids and the like. Inorganic salts include phosphates, potassium salts, sulfates, magnesium salts and the like. If necessary, iron salts, calcium salts, manganese salts, etc., may be added in the medium. Micronutrients include yeast extract and various vitamins.

The culture medium used in the present invention may be solid or liquid. In case of using a liquid medium, although stationary culture may be applied, it is recommended to employ shaking culture or aerated spinner culture because of higher yield of the objective polysaccharide. The pH for the cultivation is not defined as far as it allows that normal growth of the microorganism and intended production of the objective polysaccharide, usually a pH of 4 to 8 is preferable. Incubation temperature is also not specified, and then usually a temperature of 20° to 35° C. is preferable. As for incubation time, a period that can maximize the yield of the objective polysaccharide is selected, and then usually a period of 1 to 7 days is preferable.

Known methods may be employed for collecting the objective polysaccharide from the culture. For instance, bacterial cells are removed from the culture by suitable means such as centrifugation or filtration, then an organic solvent such as methanol, ethanol, isopropanol, acetone or the like is added to the resulting culture to cause precipitation, then the precipitate is dissolved in water and dialyzed against water, and the dialyzateis dried by suitable means such as air drying, hot-air drying, spray drying, drum drying, vacuum drying or freeze-drying to recover the objective polysaccharide.

It is also possible to employ a method in which the substances other than the components of the objective polysaccharide are removed from the culture by ultrafiltration, and the resulting concentrated solution is dried in a manner such as mentioned above. If necessary, the obtained product may be purified by a usual way to provide a high-purity product. Various means such as ion exchange, gel filtration, various types of column chromatography such as affinity chromatography, precipitation or salting-out with a quarternized ammonium salt, precipitation by use of an organic solvent, etc., may be employed for the purification.

The degree of polymerization of the polysaccharide of the present invention can be varied by adjusting the culture medium composition or the conditions of the collecting operations. It is also possible to hydrolyze the collected product or the purified product by using TFA, formic acid, hydrochloric acid or the like while adjusting the operating conditions. Thus, the molecular weight of the polysaccharide of the present invention can be freely adjusted within the range of approximately $5\times10^3$ to $10\times10^6$.

The polysaccharide of the present invention has gel-forming properties, moisture retainability, film-forming properties and other useful properties. Especially regarding gel-forming properties, it is notable that a native polysaccharide gels by heating and the produced gel is heat reversible, whereas a deacetylated polysaccharide has the nature that it gels in the presence of a metal salt and the formed gel is heat irreversible. Also, in comparison with gellan gum used as a gelatinizer, both the polysaccharide themselves and their gels have an excellent alkali resistance and have no water releasing tendency such as observed in the gel of curdlan. Regarding moisture retention, the present polysaccharide has the moisture retaining property which is little affected by the ambient humidity as compared with that of sodium hyaluronate which is a primary example of moisture retaining agent. In terms of gel-forming properties and moisture retention, a polysaccharide with a molecular weight of about $10^5$ to $10^6$ is preferably used.

The polysaccharide of the present invention can be molded into a colorless and transparent tough film by casting a 2% (w/v) aqueous solution of the said polysaccharide uniformly on a flat plate, and evaporating water. Such film forming ability of the present polysaccharide warrants its effective application as a packaging film material or a film forming agent such as a coating agent. Further, the polysaccharide of the present invention can be used for the preparation of emulsifier, foam stabilizer, water retaining agent and cement admixture as described in the Examples given below.

BEST MODE FOR CARRYING OUT THE INVENTION

The present invention is described in further detail below. The examples are not to be construed as limiting the scope of the invention.

Example 1

(Preparation of polysaccharide)

The medium of the composition (100 ml) listed in Table 5 was put into a 500 ml Sakaguchi's flask, and after 20-minute moist heat sterilization at 121° C., one platinum loop of the slant-cultured Agrobacterium radiobacter TNM-2 strain (FERM BP-4393) was implanted in the medium and the reciprocal shaking culture was carried out at a shaking frequency of 110 strokes per minute at 28° C. for 2 days.

TABLE 5

| Medium composition (wt %) | |
| --- | --- |
| Sucrose | 4% |
| Sodium nitrate | 0.1% |

TABLE 5-continued

| Medium composition (wt %) | |
| --- | --- |
| Potassium monohydrogenphosphate | 0.1% |
| Magnesium sulfate heptahydrate | 0.05% |
| Iron sulfate heptahydrate | 0.001% |
| Yeast extract | 0.4% |
| pH | 7 |

The resultant culture (60 ml) was inoculated into a 10 liters jar fermentor in which 6 liters of a medium of the same composition as listed in Table 5 had been placed and sterilized in the same way as described above, and the aerated spinner culture was carried out under the conditions of 28° C. and aeration rate of 6 liter/min for 94 hours. The spinning speed was 200 r.p.m. during the initial 19-hour period of cultivation, 300 r.p.m. in the succeeding period from the 20th to the 51st hour of cultivation, 350 r.p.m. in the period from the 52nd to the 70th hour of cultivation, and 400 r.p.m. thereafter.

The resulting culture was diluted 2-fold with water and centrifuged to remove the bacterial cells. The cross-flow ultrafiltration of the supernatant of the solution was repeatedly carried out until the substances (such as residual medium ingredients) other than the specified components of the objective polysaccharide were removed. An ultrafiltration system "UF-LMS-II" (mfd. by Toyo Soda Co., Ltd.) (differential molecular weight: $3\times10^6$) was used for the ultrafiltration. The above concentrated solution which did not pass through the ultrafiltration membrane was freeze-dried to obtain about 17 g of a single polysaccharide per one liter of the medium. The singleness of the product polysaccharide was confirmed by high-speed-high performance liquid chromatography of GPC mode.

The molecular weight of the obtained polysaccharide was determined by high-speed-high performance liquid chromatography with a column of "Asahipak GFA-7MF" (mfd. by Asahi Chemical Industry Co., Ltd.) using a 0.1M $NaNO_3$ solution as mobile phase. The retention time of the peak top on the chromatogram of the polysaccharide showed a value corresponding to a molecular weight of about $2\times10^6$ on the molecular weight-retention time calibration drawn by using pullulan of a known molecular weight as standard sample.

The said polysaccharide was hydrolyzed into the constituent saccharides and the liquid chromatographical analysis of the hydrolyzates was carried out in the form as they are and the liquid chromatographical analysis after fluorescent labeling was carried out again. From the previously drawn calibration curves and the contents of the respective constituent saccharides determined from the peak heights of the respective saccharides in the measurements, the molar ratio of the constituent saccharides was determined to be as follows: D-glucose:D-galactose:D-glucuronic acid:D-ribose:D-riburonic acid=10.0:2.1:2.0:1.0:0.9. The polysaccharide was deacylated in an aqueous solution of 0.01M KOH and 0.13M KCl at room temperature for 6 hours and then the high-speed liquid chromatographic analysis was carried out. There was detected a peak with the same retention time as the peak observed in the analysis of the potassium acetate solution. From the calibration previously drawn from the analysis of a potassium acetate solution and the peak height in the measurement, the o-acetyl group content in the polysaccharide was 8% by weight based on the whole polysaccharide.

Example 2

(Preparation of polysaccharide)

The medium of the composition (100 ml) listed in Table 6 was put into a 500 ml Sakaguchi's flask, and after 20-minute moist heat sterilization at 121° C., one platinum loopful of slant-cultured Agrobacterium radiobacter TNM-2 strain was implanted in the medium and the reciprocal shaking culture was carried out at a shaking frequency of 110 strokes per minutes at 28° C. for 2 days.

TABLE 6

| Medium composition (wt %) | |
| --- | --- |
| Sucrose | 2% |
| Sodium nitrate | 0.2% |
| Potassium monohydrogenphosphate | 0.1% |
| Magnesium sulfate heptahydrate | 0.05% |
| Iron sulfate heptahydrate | 0.001% |
| Yeast extract | 0.05% |
| pH | 6 |

The obtained culture (60 ml) was inoculated into a jar fermentor in which 6 liters of a medium of the same composition as listed in Table 6 was contained and sterilized in the same way as described above, and after adding 0.05% by weight of potassium chloride, the aerated spinner culture of said cultured bacterial strain was carried out at an aeration rate of 6 liter/min for 125 hours. The temperature was set at 28° C. during the initial 85-hour period of cultivation and raised to and kept at 35° C. in the rest of the cultivation operation, while the spinning speed was set at 300 r.p.m. during the initial 72-hour period of cultivation and raised to and kept at 800 r.p.m. thereafter.

And then the same treatments as in Example 1 were carried out to give about 9 g of a single polysaccharide per one liter of the medium. The molar ratio of the constituent saccharides and the o-acetyl group content were determined by the same way as in Example 1. The molar ratio was as follows: D-glucose:D-galactose:D-glucuronic acid:D-ribose:D-riburonic acid=10.0:1.9:2.4:0.7:1.2, and the o-acetyl group content was 8% by weight. Also, the molecular weight of the obtained polysaccharide was $2.6 \times 10^6$.

Example 3

(Preparation of polysaccharide)

The medium (100 ml) same as used in Example 2 was put into a 500 ml Sakaguchi's flask, and after 20-minute moist heat sterilization at 121° C., one platinum loop of slant-cultured Agrobacterium radiobacter TNM-2 strain was implanted in the medium and the reciprocal shaking culture was carried out at a shaking frequency of 110 strokes per minute at 28° C. for 5 days.

The obtained culture was diluted 2-fold with water, adjusted to pH 13 with a 10M sodium hydroxide solution and centrifuged to remove the bacterial cells. Thrice as much amount (v/w) of ethanol was added to the supernatant solution, and the formed precipitate was dissolved in water and dialyzed against current water for 2 days. The dialyzate was freeze-dried to obtain about 2 g of a single polysaccharide per liter of the medium. The molar ratio of the constituent saccharides of the obtained polysaccharide and the content of o-acetyl groups were determined by the same way as in Example 1. The results were as follows: D-glucose:D-galactose:D-glucuronic acid:D-ribose:D-riburonic acid=10.0:2.0:1.9:1.2:0.7; o-acetyl group content=0% by weight; molecular weight=$4.3 \times 10^6$.

Example 4

(Preparation of polysaccharide)

The procedure of Example 3 was carried out except for use of a medium having a composition of 4 wt % sucrose, 0.2 wt % polypeptone, 0.1 wt % yeast extract and 0.1 wt % meat extract and a pH of 7 to obtain about 3 g of a single polysaccharide per liter of the medium. The molar ratio of the component saccharides of the obtained polysaccharide and the content of o-acetyl groups were as follows: D-glucose:D-galactose:D-glucuronic acid:D-ribose:D-riburonic acid=10.0:2.2:2.3:0.9:1.0; o-acetyl group content= 5% by weight. The molecular weight of the polysaccharide was $3.5 \times 10^6$.

Example 5

(Preparation of polysaccharide)

The procedure of Example 2 was carried out except for changes of the content of sucrose in the medium composition to 4% by weight, the jar fermentor speed to 400 r.p.m. and the incubation temperature in the jar fermentor to 28° C. to obtain about 3 g of a single polysaccharide per liter of the medium. The molar ratio of the component saccharides of the obtained polysaccharide and the content of o-acetyl groups were as follows: D-glucose:D-galactose:D-glucuronic acid:D-ribose:D-riburonic acid= 10.0:2.5:2.0:0.8:1.0; o-acetyl group content=7% by weight. The molecular weight of the polysaccharide was $2.3 \times 10^6$.

Example 6

(Evaluation of storage stability and acid and alkali resistance of the polysaccharide)

The polysaccharide obtained in Example 5 (molecular weight: approx. $2 \times 10^6$), gellan gum (molecular weight: $5.9 \times 10^5$, produced by Kelco Corp.), sodium hyaluronate derived from cockscomb (molecular weight: $1.7 \times 10^6$, produced by Cupie Corp.) and sodium hyaluronate produced by microbial fermentation (molecular weight: $1.7 \times 10^6$, produced by Denki Kagaku Kogyo Co., Ltd.) were dissolved respectively in each of water, 0.1M HCl and 0.1M NaOH to a concentration of 0.2% (w/v) and kept in a closed vessel at 50° C. for one month. The change of molecular weight after storage was examined by high-speed-high performance liquid chromatography. The results are listed in Table 7.

TABLE 7

| Solvent | Polysaccharide of this invention (Example 5) | gellan gum | Sodium hyaluronate derived from cockscomb | Sodium hyaluronate produced by microbial fermentation |
| --- | --- | --- | --- | --- |
| <Molecular weight after storage> | | | | |
| Water | $2.3 \times 10^6$ | $1.6 \times 10^5$ | $1.6 \times 10^6$ | $1.6 \times 10^6$ |
| 0.1 M HCl | $1.4 \times 10^6$ | Gelation | $1.6 \times 10^4$ | $1.7 \times 10^4$ |
| 0.1 M NaOH | $2.3 \times 10^6$ | Perfectly degraded | Perfectly degraded | Perfectly degraded |

As is seen from the above results, any of the tested compounds showed no noticeable change of molecular weight when they were dissolved in water. However, when the tested compounds were dissolved in 0.1M HCl and kept in this state, gellan gum gelled and the molecular weight of sodium hyaluronate was reduced to about 1/100, while the polysaccharide of the present invention was substantially unchanged in molecular weight. Also, when the tested compounds were dissolved in 0.1M NaOH and kept in this state, gellan gum and sodium hyaluronate were degraded to the constituent saccharides while the polysaccharide of the present invention was not degraded at all. This fact means that the polysaccharide of the present invention is a chemically more stable substance than gellan gum and sodium hyaluronate.

Example 7

(Evaluation of viscosity of polysaccharide)

The polysaccharide obtained in Example 1 was dissolved in water to prepare the aqueous solutions with concentrations of 0.1%, 0.2%, 0.5% and 1.0% (w/v), respectively. The viscosity of each aqueous solution at room temperature was measured using a B type viscometer at 60 r.p.m.. By way of the comparison, viscosities of the aqueous solutions of xanthan gum (Kelzan produced by Kelco Corp.) with said concentrations were also measured. As is seen from the results listed in Table 8, the polysaccharide of the present invention has a viscosity suited for practical use.

TABLE 8

| Concentration % (w/v) | Polysaccharide of this invention (cp) | Xanthan gum (cp) |
|---|---|---|
| 0.1 | 15 | 50 |
| 0.2 | 35 | 100 |
| 0.5 | 200 | 400 |
| 1.0 | 1,000 | 1,100 |

Example 8

(Evaluation of viscosity of polysaccharide)

The viscosity of a 1% (w/v) aqueous solution of the polysaccharide of this invention prepared in Example 7 was measured by using a B type viscometer at 6, 12, 30, and 60 r.p.m. at room temperature. By way of comparison, the viscosity of a similar aqueous solution of xanthan gum (Kelzan produced by Kelco Corp.) was also measured under the same conditions. As is seen from the results listed in Table 9, the polysaccharide of the present invention has a viscosity suited for practical use.

TABLE 9

| Rotary speed (rpm) | Polysaccharide of this invention (cp) | Xanthan gum (cp) |
|---|---|---|
| 6 | 4,000 | 9,400 |
| 12 | 3,000 | 5,100 |
| 30 | 1,600 | 1,600 |
| 60 | 1,000 | 1,100 |

Example 9

(Evaluation of viscosity of polysaccharide)

The polysaccharide obtained in Example 1 was dissolved in 0.1M HCl, 0.001M HCl, 0.1M NaOH, 0.001M NaOH and water to prepare the 1% (w/v) solutions, and the viscosities of these solutions at room temperature were measured by using a B type viscosity at 60 r.p.m. As is seen from the results listed in Table 10, the viscosity of the polysaccharide solution in the present invention is not varied greatly in the acid and alkaline media.

TABLE 10

| | Viscosity (cp) |
|---|---|
| 0.1 M Hcl | 700 |
| 0.001 M Hcl | 1,000 |
| 0.1 M NaOH | 800 |
| 0.001 M NaOH | 1,000 |
| Water | 1,000 |

Example 10

(Evaluation of viscosity of polysaccharide)

The viscosities of a 1% (w/v) aqueous solution of the polysaccharide obtained in Example 1 were measured by using a B type viscometer at 60 r.p.m. at 5° C., 25° C., 50° C. and 90° C. The results are listed in Table 11, which indicate that the polysaccharide of the present invention has the property that its viscosity rises at low temperatures and lowers at high temperatures.

TABLE 11

| Temperature (°C.) | Viscosity (cp) |
|---|---|
| 5 | 1,250 |
| 25 | 1,000 |
| 50 | 700 |
| 90 | 300 |

Example 11

(Evaluation of viscosity of polysaccharide)

NaCl or $CaCl_2$ was added to a 1% (w/v) aqueous solution of the polysaccharide obtained in Example 1 with the concentrations of 0.5%, 1.0%, 10% and 20% (w/v), and viscosity at room temperature of the respective aqueous solutions was measured by using a B type viscometer at 60 r.p.m. at room temperature. As is seen from the results listed in Table 12, viscosity of the polysaccharide of the present invention stays constant even in the presence of a high-concentration salt.

TABLE 12

| | Viscosity (cp) |
|---|---|
| No addition | 1,000 |
| NaCl 0.5% (w/v) | 800 |
| 1.0% | 850 |
| 10% | 900 |
| 20% | 1,000 |
| $CaCl_2$ 0.5% (w/v) | 800 |
| 1.0% | 800 |
| 10% | 800 |
| 20% | 800 |

Example 12

(Preparation of gel)

A 2% (w/v) aqueous solution of the polysaccharide obtained in Example 5 was boiled with stirring for 5 minutes and then cooled at room temperature. The soft and stable heat-reversible gel was obtained.

Example 13

(Evaluation of water, acid and alkali resistance of gel)

The gel obtained in Example 12 and a gel of gellan gum prepared in accordance with Example 12 were respectively put into water, 1M HCl and 1M NaOH and allowed to stand for 30 hours. When the samples were stood in water and 1M HCl, each of said gels remained neither dissolved nor disintegrated. When the samples were stood in 1M NaOH, the gel of gellan gum was dissolved and disintegrated in one-hour standing, but the gel of the polysaccharide of the present invention maintained the original form even after 30 hours of standing. Thus, the polysaccharide of the present invention is superior to gellan gum in that it is capable of forming an alkali-resistant gel.

Example 14

(Evaluation of water absorptivity of gel)

An 8.2 g of the gel obtained in Example 12 was left in water for 3 days. The gel absorbed water and its weight increased to about 99 g.

Example 15

(Evaluation of water absorptivity of gel)

An 8.2 g of the gel obtained in Example 12 was dried in a chamber to obtain 0.44 g of dry gel and this dry gel was immersed in water. The dry gel immediately absorbed water and restored the original state.

Example 16

(Evaluation of Syneresistic nature of gel)

A 2% (w/v) aqueous solution of the polysaccharide obtained in Example 5 and a 2% (w/v) water suspension of curdlan (produced by Wako Pure Chemical Industry Co., Ltd.) were boiled for 5 minutes and then cooled at room temperature to form gels. After keeping each gel at 4° C. for 20 hours, the water release percentage of each gel was measured. The water release percentage of the curdlan gel was 21% while that of the gel of the polysaccharide of the present invention was 2%. Thus, the gel of the polysaccharide of the present invention is lower in water release percentage than the curdlan gel. In the present invention, the water release percentage is defined as follows:

Water release percentage (%)=(C−D)/C×100 wherein C is total gel weight before storage and D is total gel weight after storage.

Example 17

(Evaluation of utility of polysaccharide for cell culture)

The polysaccharide obtained in Example 5 was added to an Eagle MEM medium for cell culture to a concentration of 1% by weight, and a sample was pipetted into a Petri dish and the moist heat sterilization was carried out at 121° C. for 15 minutes. Immediately before the medium solidified, the cell culture solution was added. By way of comparison, the same operation was carried out by using 0.5% by weight of agar instead of 1% by weight of the polysaccharide. The cell growth was almost equal in both the medium using the polysaccharide and the medium using agar, but the water release percentage after one week was 4% in the medium using the polysaccharide and 5% in the medium using agar.

Example 18

(Evaluation of utility of polysaccharide for microbial culture)

A medium (pH 7) composed of 2 g of the polysaccharide obtained in Example 5, 0.7 g of meat extract, 1 g of peptone, 0.3 g of sodium chloride and 100 ml of water was pipetted into a test tube and the moist heat sterilization of it was carried out at 121° C. for 20 minutes. Then the medium was cooled to room temperature to prepare a slant medium. By way of comparison, the same operation was repeated using 2 g of agar in place of 2 g of the polysaccharide. The microbial growth was equal in both the medium using the polysaccharide and the medium using agar, but the water release percentage after one week was 10% in the medium using the polysaccharide and 15% in the medium using agar. Also, the medium using agar was opaque while the medium using the polysaccharide was transparent, allowing easy perception of the state of the colony. The above results confirmed that a medium for microbial culture capable of long-time preservation can be prepared by using the polysaccharide of the present invention.

Example 19

(Evaluation of utility of polysaccharide for plant culture)

The polysaccharide obtained in Example 5 was added to a Murashige & Skoog medium to a concentration of 2% (w/v), and then the medium was pipetted into an Erlenmeyer flask, subjected to the moist heat sterilization of it was carried out for 15 minutes at 121° C. and cooled to room temperature to be solidified. By way of comparison, the same operation was carried out except for use of 2% (w/v) of agar in place of 2% (w/v) of polysaccharide. The growth of the plant was equal in both the medium using the polysaccharide and the medium using agar, but the water release percentage after three months was 15% in the medium using the polysaccharide while it was 21% in the medium using agar. Also, the medium using agar was opaque while the medium using the polysaccharide was transparent, allowing easy perception of the state of callus or root development. The above results confirmed that a medium for plant culture for long-time preservation can be prepared using of the polysaccharide of the present invention.

Example 20

(Evaluation of moisture retention of polysaccharide)

The polysaccharide obtained in Example 5 (molecular weight: $2 \times 10^6$) was put into a weighing tube, sufficiently dried in vacuum therein, then placed in a desiccator adjusted to RH 79% with $NH_4Cl$ and left therein until the weight of the polysaccharide became constant. Then the polysaccharide was transferred into a desiccator adjusted to RH 42% with $Zn(NO_3)_2 \cdot 6H_2O$ and left therein until the weight of the polysaccharide became constant. The above operations were carried out at a constant temperature of 20° C. For comparing moist retention, the same operation was repeated using sodium hyaluronate derived from cockscomb (molecular weight: approx. $2 \times 10^6$, produced by Cupie Corp.) and sodium hyaluronate produced from microbial fermentation (molecular weight: approx. $2 \times 10^6$, produced by Denki Kagaku Kogyo Co., Ltd.).

The moisture retention percentage under the designated relative humidity conditions was calculated from the following equation:

Moisture retention percentage (%)=(A−B)/B×100 wherein A is the sample weight when it became constant under the designated relative humidity conditions, and B is the dry sample weight. The results of evaluation of moisture retention are listed in Table 13.

TABLE 13

|  | Polysaccharide of this invention | Sodium hyaluronate derived from cockscomb | Sodium hyaluronate produced from microbial fermentation |
|---|---|---|---|
|  | <Moisture retention percentage> | | |
| RH 79% | 30 | 45 | 42 |
| RH 42% | 21 | 30 | 30 |
| <Difference in moisture retention percentage> | 9 | 15 | 12 |

As is seen from the above results, each compound has the generally required level of moisture retention (10–50%) under an ordinary environmental condition with RH of 40–80%. However, the influence by the change of relative humidity differs among the compounds; the difference in moisture retention percentage between RH 79% and RH 42% is 15% in the case of sodium hyaluronate derived from cockscomb and 12% in the case of sodium hyaluronate produced from microbial fermentation while the difference is only 9% in the case of the polysaccharide of the present invention. Evidently, the humectant comprising the polysaccharide of the present invention is superior to said types of sodium hyaluronate in that it is less susceptible to the change of relative humidity.

Example 21

(Evaluation of film-forming properties of polysaccharide)

A 2% (w/v) aqueous solution of the polysaccharide obtained in Example 5 was cast into a template (50×50×1 mm) on a PET sheet and dried at 50° C. to mold a film. By way of comparison, a film was molded in the similar way using pullulan ("Pullulan PI-20" produced by Hayashibara Biochemical Research Center Co., Ltd.) instead of the polysaccharide. Tensile strength and elongation at break of the molded films were measured by using a precision universal testing machine (AGS-500B mfd. by Shimadzu Corp.). As is seen from the results listed in Table 14, the film molding obtained from the polysaccharide of the present invention has a sufficient tensile strength and elongation at break in practical use.

TABLE 14

|  | Polysaccharide of this invention | Pullulan |
|---|---|---|
| Tensile strength (kg/cm$^2$) | 400 | 500 |
| Elongation at break (%) | 6 | 3 |

Example 22

(Evaluation of emulsion stability of polysaccharide)

A 35 g of salad oil was added gradually to 35 g of a 1% (w/v) aqueous solution of the polysaccharide obtained in Example 5 with stirring by a homomixer at 10,000 r.p.m.. Stirring was continued for 5 minutes to emulsify the salad oil and the emulsion was allowed to stand. By way of comparison, the same operation was carried out using carrageenan (CP Gum FA, trade name, available from Dai-Nippon Pharmaceutical Co., Ltd.) instead of the polysaccharide. In both cases, a white creamy emulsion was formed immediately after emulsification. However, in the case of the emulsion formed by using carrageenan, an aqueous phase appeared after standing for 24 hours, and the height of the aqueous phase reached approximately 30% of the overall height of the solution after standing for 120 hours. On the other hand, in the case of the emulsion formed by using the polysaccharide, there was observed no trace of phase separation even after standing for 120 hours. These facts confirmed the emulsion stability of the polysaccharide of the present invention for salad oil is better than that of than carrageenan.

Example 23

(Evaluation of foam stability in milk of polysaccharide)

A 1 g of the polysaccharide obtained in Example 5 was added to 100 ml of cow's milk and stirred by a homomixer at 10,000 r.p.m. to form foams. For the purpose of comparison, the same operation was carried out using carrageenan (CP Gum FA) in place of the polysaccharide. After the operation, the volume increase was 33% in case the polysaccharide of the present invention was used, but the volume increase was 10% in case carrageenan was used. Also, in the case of carrageenan, the foams disappeared after standing for 24 hours, but in the case of the polysaccharide of the present invention, the foams existed stably after standing for 24 hours.

Example 24

(Evaluation of foam stability in ice cream of polysaccharide)

First, 1,000 g of cow's milk was put into a 3-liter stainless steel vat placed in a 70° C. hot water bath and stirred by a stirrer. Then, 120 g of powdered skim milk, 130 g of sugar and 5 g of the polysaccharide obtained in Example 5 were added to the milk with stirring, followed by further successive addition of 250 g of whole-fat condensed milk, 200 g of raw cream (milk fat content: 40%), 100 g of yolk and 2 g of vanilla essence to prepare a mix. This mix was kept at 80° C. for 10 minutes, then homogenized and frozen. When the temperature became −3° C., the mix was sampled to obtain a vanilla ice cream specimen with a milk fat content of 14.0% and a no-fat milk solid content of 13.0%. By way of comparison, the same operation was carried out using 5 g of carrageenan (CP Gum FA) instead of 5 g of the polysaccharide to prepare a comparative ice cream specimen.

Overrun of each specimen of ice cream was measured. It was calculated from the measured values of weight of 100 ml of the mix immediately before freezing and 100 ml of ice cream immediately after freezing. A 100 ml plastic container was used for the measurement of weight. Overrun of the ice cream specimen using carrageenan was 35% and that using the polysaccharide was 51%.

Example 25

(Evaluation of water retention in jelly of polysaccharide)

A mixed solution of 1 wt % of the polysaccharide obtained in Example 5, 2 wt % of a 10 wt % aqueous citric acid, 0.7 wt % of a 10 wt % aqueous trisodium citrate, 20 wt % of sugar, 0.1 wt % of grape flavor, 0.14 wt % of colorant and the balance of water was boiled for 5 minutes and then, after filled in a cup, cooled to gel. By way of comparison, the same operation was carried out using 1 wt % of agar instead of 1 wt % of the polysaccharide. Each of the obtained specimens of jelly was kept at 4° C. for 20 hours and then the water release percentage was measured. The water release percentage of the jelly using the polysaccharide was 2% while that of the jelly using agar was 4%.

Example 26

(Evaluation of water retention in sponge cake of polysaccharide)

The polysaccharide obtained in Example 5 was added to a cake mix so that the content of the polysaccharide would become 0.5 wt %, and water was added to prepare a dough, which was then baked in an oven. By way of comparison, the same operation was repeated using 0.5 wt % of carrageenan (CP Gum FA) instead of 0.5 wt % of the polysaccharide to obtain a sponge cake. Each sample of sponge cake was kept at -20° C. for 24 hours and its water release percentage was measured. The water release percentage was 2% in the case of the sponge cake using the polysaccharide and 10% in the case of the sponge cake using carrageenan.

Example 27

(Evaluation of thickening and water retention in cement of polysaccharide)

A 50 g of Portland cement (produced by Sumitomo Cement Co., Ltd.) was added to (1) 25 ml of a 0.2% (w/v) aqueous solution of the polysaccharide obtained in Example 5, (2) 25 ml of a 0.1M NaOH solution containing 1% (w/v) of curdlan, and (3) 25 ml of water, respectively, and mixed with stirring. Each sample of cement slurry (20 g) was put into a plastic Petri dish (90 mm in diameter and 15 mm high) and the dish was vibrated to spread the cement slurry over the whole dish. Immediately thereafter, the dish was erected vertically and left in this state, causing the hardening of the cement slurry. This operation was carried out at room temperature. After the cement slurry has been hardened, the hardened cement thickness at the upper, middle and lower portions of the vertically erected dish was measured. As is seen from the results shown in Table 15, it is possible to prevent run-down of cement slurry by adding the polysaccharide of the present invention.

TABLE 15

| | Upper portion (mm) | Middle portion (mm) | Lower portion (mm) |
|---|---|---|---|
| Hardened cement containing polysaccharide | 3 | 3 | 4 |
| Hardened cement containing curdlan | 3 | 3 | 6 |
| Hardened cement containing water | 2 | 2 | 10 |

Example 28

(Property-improving effect of polysaccharide in hydraulic compositions)

There were prepared the hydraulic compositions of the formulation listed in Table 16, one blended with the polysaccharide obtained in Example 5 and the other blended with curdlan (produced by Wako Pure Chemical Industry Co., Ltd.) as admixture, and the slump flow value, which is an index of fluidity, and compression strength of the compositions when worked into ferro-concrete were measured. The results are listed in Table 16. Ferroconcrete was made by placing concrete in a mold where the reinforcing bars were arranged at minimal intervals of 35 mm, and compression strength was measured after aging of 6 days, 7 days and 28 days. From the results listed in Table 16 it is recognized that the properties of the hydraulic compositions are improved by the addition of the polysaccharide of the present invention. In the table, the figures in the parentheses indicate wt % based on the binding materials (cement, blast furnace slag and fly ash). A formalin naphthalinsulfonate high condensate was used as the high-performance water reducing agent, and a lignin sulfonic acid compound-polyol composite was use as an AE water reducing agent.

TABLE 16

| | Polysaccharide blended cement | curdlan blended cement |
|---|---|---|
| <Formulation (parts by weight)> | | |
| Water | 150 | 150 |
| Cement | 150 | 150 |
| Blast furnace slag | 150 | 150 |
| Fly ash | 200 | 200 |
| Fine aggregate | 660 | 660 |
| Coarse aggregate (maximal size: 20 mm) | 940 | 940 |
| High-performance water-reducing agent | 5 (1) | 5 (1) |
| AE water reducing agent | 0.75 (0.15) | 0.75 (0.15) |
| Polysaccharide | 1.5 (0.3) | 0 |
| Curclan | 0 | 1.5 (0.3) |
| Slump flow (cm) | 50 | 48 |
| Compression strength (Kgf/cm$^2$) Age | | |
| 6 days | 287 | 285 |
| 7 days | 288 | 286 |
| 28 days | 428 | 427 |

Industrial Applicability

According to the present invention described above, it is possible to produce efficiently a novel polysaccharide which has high compatibility with the global environments and can be used as gelatinizer, humectant, film-forming agent, emulsifier, foam stabilizer, water retaining agent, cement admixture, etc., in many fields of industries. Especially in use of the polysaccharide as a gel-forming agent and a humectant, the problems of the conventional products are eliminated.

What is claimed is:

1. A novel polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

2. A process for producing a polysaccharide which comprises culturing a microorganism belonging to the genus Agrobacterium and having an ability to produce a polysaccharide comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight, and collecting from the culture a polysaccharide comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

3. The process according to claim 2, wherein the microorganism is Agrobacterium radiobacter TNM-2 strain (Accession No. FERM BP-4393).

4. The process according to claim 2, wherein the microorganism is Agrobacterium radiobacter TNM-2 strain (Accession No. FERM BP-4393) or a variant thereof that can produce the polysaccharide.

5. A gelatinizer comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

6. A humectant comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

7. A film-forming agent comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

8. An emulsifier comprising a polysaccharide having a molecular weight of about $5 \times 10^3$ to $10 \times 10^6$ as measured by gel permeation chromatography and comprising 5 saccharides selected from the group, consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

9. A foam stabilizer comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

10. A water-retaining agent comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

11. A cement admixture comprising a polysaccharide having a molecular weight of about $5 \times 10^3$ to $10 \times 10^6$ as measured by gel permeation chromatography and comprising 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

12. Agrobacterium radiobacter TNM-2 strain (Accession No. FERM BP-4393), or its variants that can produce a polysaccharide that comprises 5 saccharides selected from the group consisting of D-glucose, D-galactose, D-glucuronic acid, D-ribose and D-riburonic acid, in a molar ratio of 10:1.8–2.9:1.8–2.6:0.5–1.7:0.5–1.7 (D-glucose:D-galactose:D-glucuronic acid:D-ribose:D-riburonic acid), with the content of o-acetyl groups in the polysaccharide being 0–10% by weight.

* * * * *